United States Patent [19]

Dorsett et al.

[11] Patent Number: 4,949,710
[45] Date of Patent: Aug. 21, 1990

[54] METHOD OF ARTIFACT REJECTION FOR NONINVASIVE BLOOD-PRESSURE MEASUREMENT BY PREDICTION AND ADJUSTMENT OF BLOOD-PRESSURE DATA

[75] Inventors: Thomas J. Dorsett, Hillsboro; Charles L. Davis, Portland, both of Oreg.

[73] Assignee: Protocol Systems, Inc., Oreg.

[21] Appl. No.: 254,204

[22] Filed: Oct. 6, 1988

[51] Int. Cl.$^5$ .......................................... A61B 5/0225
[52] U.S. Cl. ..................................... 128/680; 128/682; 128/681
[58] Field of Search .......................... 128/672, 677-686

[56] References Cited

U.S. PATENT DOCUMENTS

| | | |
|---|---|---|
| 3,791,378 | 2/1974 | Hochberg et al. |
| 4,174,707 | 11/1979 | Link et al. ............................ 128/681 |
| 4,263,918 | 4/1981 | Swearingen et al. ............... 128/681 |
| 4,349,034 | 9/1982 | Ramsey, III . |
| 4,360,029 | 11/1982 | Ramsey, III . |
| 4,367,751 | 1/1983 | Link et al. . |
| 4,543,962 | 10/1985 | Medero et al. ...................... 128/682 |
| 4,546,775 | 10/1985 | Medero ........................... 128/680 X |
| 4,638,810 | 1/1987 | Ramsey, III et al. ......... 128/682 X |
| 4,703,760 | 11/1987 | Miyawaki et al. .................. 128/681 |
| 4,754,761 | 7/1988 | Ramsey, III et al. .......... 128/681 X |
| 4,796,184 | 1/1989 | Bahr et al. ...................... 128/682 X |

*Primary Examiner*—Angela D. Sykes
*Attorney, Agent, or Firm*—Kolisch, Hartwell & Dickinson

[57] ABSTRACT

For use in performing non-invasive blood-pressure measurement (NIBP), an artifact rejection method for predicting expected data values from acquired data, and for adjusting previously acquired data based on the relationship of actually measured data values to their corresponding predicted values. The method is practiced in a system comprising an inflatable, occluding cuff, a pump and a valve coupled to the cuff, and monitoring apparatus coupled to the cuff adapted to measure cuff pressure and recurring blood-pressure pulsations occurring in the cuff that are caused by each heart contraction occurring in a measurement cycle. Cuff pressure is raised to a level above the patient's systolic pressure, and progressively reduced in a stepwise fashion to an ending cuff pressure. A fixed number of pulsations are measured and processed at a first and second cuff-pressure step, and a generally lesser number of pulsations are measured and processed at a third and subsequent cuff-pressure steps. The method includes, at the second cuff-pressure step, generating a prediction curve for predicting a next, expected-to-be-stored pulsation data value for a next, lower cuff-pressure step. The method also includes repeatedly smoothing the prediction curve based on the difference between a pulsations's calculated data value and its respective predicted data value. A final, smoothed curve is generated reflecting a final pulsation data value for each cuff-pressure step. From the final curve, the desired blood pressure parameters are derived and displayed in the form of arabic numerals by means of an LCD read-out.

19 Claims, 4 Drawing Sheets

METHOD OF ARTIFACT REJECTION FOR NONINVASIVE BLOOD-PRESSURE MEASUREMENT BY PREDICTION AND ADJUSTMENT OF BLOOD-PRESSURE DATA

BACKGROUND AND SUMMARY OF THE INVENTION

This invention pertains to an improvement in artifact rejection methods for noninvasive blood-pressure measurement, and more particularly, to a unique method of predicting, from acquired data, subsequent, expected data values.

Examples of artifact rejection methods for noninvasive blood-pressure measurement in the closest prior art are disclosed in U.S. Pat. No. 4,367,751 to Link, et al. and U.S. Pat. No. 4,543,962 to Medero, et al.

In the typical practice of an oscillometric, noninvasive blood-pressure measurement method with a person, a counterpressure-producing cuff is wrapped around the person's upper arm, with the cuff then inflated to a counterpressure above systolic pressure to occlude an artery (blood vessel) in the arm. Thereafter cuff counterpressure is progressively reduced in a stepped fashion from this suprasystolic pressure to an ending counterpressure where the cuff is substantially deflated. During progressive reduction of cuff counterpressure, the artery opens progressively from an occluded state to an unoccluded state.

During the change from the occluded state to the unoccluded state, the artery begins to product detectable pulsations against the cuff, and the waveforms of these pulsations are monitorable to produce graphic illustrations of blood-pressure parameters. As is well-known to those skilled in the art in handling blood-pressure measurements, the pulsations just referred to increase in amplitude toward a maximum as cuff counterpressure decreases below systolic pressure, and then decrease in amplitude. By categorizing these pulsations relative to their occurrences in time and to their respective amplitudes, desired blood-pressure parameters are determined.

In all methods of acquiring usable blood-pressure data, it is important to detect, and reject, as faithfully as possible, pressure "artifacts" which are not induced by blood-pressure pulsations. Artifacts occur, for example, where a subject moves, changes muscle tension, etc.

The method of the present invention significantly addresses this key issue.

An important object of the invention, therefore, is to provide for artifact rejection in a unique way which ensures that accepted pressure waveforms truly are blood-pressure induced.

Another object is to decrease the number of pressure waveforms that are monitored at each cuff counterpressure level, thereby to decrease the overall time period of a measuring cycle, thus to maximize efficiency.

By way of introduction, applicants' novel artifact rejection method is disclosed as being practiced in conjunction with an "impulse-based method" of non-invasive blood-pressure measurement (NIBP). This "impulse-based method" of NIBP is fully disclosed in a prior-filed patent application, Ser. No. 07/198,468, filed May 25, 1988, by Craig H. Nelson, Thomas J. Dorsett and Charles L. Davis, for "METHOD FOR NONINVASIVE BLOOD-PRESSURE MEASUREMENT BY EVALUATION OF WAVEFORM-SPECIFIC AREA DATA".

It should be understood that while the present invention is being disclosed in the measurement setting described in the above-referenced patent application, in which setting the invention has been shown to offer particular utility, the invention can also be used in a variety of blood pressure measurement systems which acquire blood-pressure data in different ways. For example, a number of systems are currently available wherein blood pressure parameters are derived from monitoring the amplitudes rather than the impulses characterizing blood pressure induced waveforms.

To deal with the issue of false "artifact" data according to the method of, the present invention, a rejection technique is employed which verifies that developed blood pressure data values are proper values by employing what might be thought of as "pulse-prediction" and "pulse-adjustment".

The theory applied by applicants in carrying out their unique artifact rejection method is based on what is known in the art, and what will be described as, "Kalman Filter theory." Applicants used an algorithm based on the "Kalman Filter" to provide for what will be described as "pulse-prediction." Further, applicants applied what is known in the art as "fixed lag smoothing" to provide for what will be described as "pulse-adjustment."

Applying this theory, the present invention is employed after development of waveform data values for a predetermined number of cuff counterpressure levels at the beginning of a measuring cycle. Specifically, the technique is used to predict a next, expected-to-be-encountered data value for a next, lower cuff counterpressure level. Employing prediction for successive, next, lower cuff counterpressure levels provides a simple and accurate method of artifact rejection which also substantially decreases the number of pressure waveforms required to be monitored at a given cuff counterpressure level. Therefore, if a next, developed waveform data value for a measured waveform is within experimentally set upper and lower bounds of its corresponding predicted value, the measured value is accepted as being blood-pressure induced.

This important feature of ongoing next-to-be-expected data value prediction, significantly enhances the likelihood that a false data pulse will be rejected as an artifact.

Using the prediction technique just described for subsequent cuff counterpressure levels, it will generally be necessary to monitor only one pressure waveform at a given cuff counterpressure level. As will be explained, if the first pressure waveform which is monitored does not have a data value that is within the upper and lower bounds of its corresponding predicted value, subsequent waveforms will be monitored until one is found which does meet the boundary conditions. This situation, of "looking" for successive, subsequent "boundary-meeting" waveforms, continues only for a predetermined ultimate time interval, after which, if no proper waveform is found, the method of the invention aborts the measurement cycle.

In addition, and further in accordance with special features of the invention, the proposed rejection technique is employed further to perform a "pulse-data adjustment". Thus, the technique adjusts previously encountered (and stored) waveform data values based on the difference between a measured waveform data value and a corresponding predicted waveform data value for a given cuff counterpressure level. This is referred to herein as a "smoothing" technique. By adjusting previously stored values, smoothing provides further ensurance of the accuracy of ultimately derived, desired blood-pressure parameters.

These and other objects and advantages which are attained by the invention will become more fully apparent as the description that now follows is read in conjunction with the accompanying drawings and computer program flow charts.

DETAILED DESCRIPTION OF THE PREFERRED MANNER OF PRACTICING THE INVENTION

Figure 1:
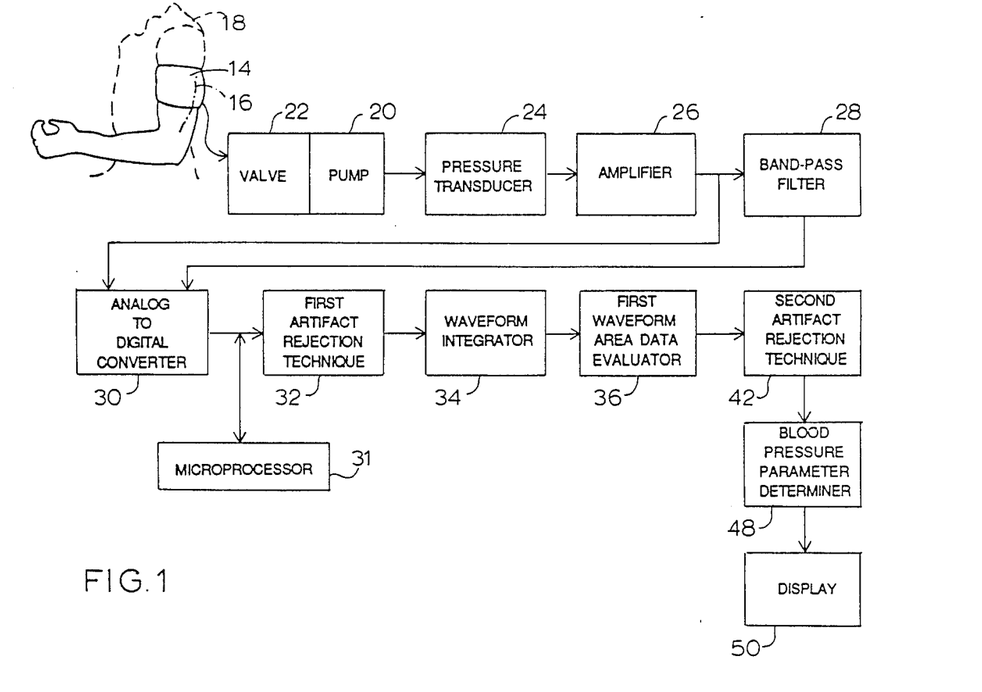
FIG. 1 is a schematic/block depiction of apparatus and software suitable for carrying out the present invention.

Turning now to FIG. 1, a schematic/block depiction of blood-pressure measuring apparatus and software characterizing applicant's NIBP system is shown. Generally describing in operational steps and in descriptions of FIG. 1's contents what is "illustrated" by this figure, cuff 14 is a means for producing a baseline counterpressure, and is disposed adjacent a blood vessel 16 (wrapped around the arm) of a living subject 18. To begin a blood-pressure measuring cycle, a pump 20 inflates cuff 14 to a point where it exerts a counterpressure against the arm that is above systolic pressure, thereby occluding vessel 16.

Under the control of a microprocessor (still to be discussed), a valve 22 progressively reduces the cuff counterpressure from the beginning counterpressure level above systolic pressure to an ending counterpressure to be described later. Preferably, counterpressure is reduced in a stepwise fashion in order to monitor pressure changes occurring in cuff 14 at each step, or cuff counterpressure level. In the preferred practice of the invention, cuff counterpressure reduces in steps of 5- to 6-mm Hg.

As the counterpressure in cuff 14 lowers, vessel 16 gradually begins to produce detectable pulsations from heart contractions. More specifically, and as previously noted, these vessel pulsations are caused by blood that has been accelerated, or given momentum, during the time period of each successive heart contraction.

At each progressively reduced counterpressure level, a pressure transducer 24 receives, at a predetermined rate, an analog pressure signal composed of a cuff counterpressure component and a pressure pulsation component which "may be" blood-pressure-induced.

Transducer 24 converts each pressure signal into an electrical signal which is amplified by an amplifier 26. The amplified electrical signal is then sent to two different locations—a band-pass filter 28, and an analog-to-digital converter 30.

Each signal is sent to filter 28 in order to have the cuff counterpressure component filtered out. The signal output of filter 28 corresponds to pressure pulsations. From filter 28, the filtered signal component is fed to converter 30 from which there emerges a first stream of digitized data which corresponds to pressure pulsations. The presently preferred monitoring interval for transducer 24 is about 5.5-msec.

Each signal from amplifier 26 is also sent to converter 30 in order to provide a second stream of data corresponding to cuff counterpressure levels at which corresponding pressure pulsations occur. Technically, the signal from amplifier 26 contains both the cuff counterpressure component and the pressure pulsation component. However, because the pressure pulsation component's value is so small relative to the cuff counterpressure component's value, we have found that the signal from amplifier 26 substantially corresponds to cuff counterpressure.

Hereafter, the second stream of data corresponding to cuff counterpressure levels will be called baseline counterpressure data.

Thus, converter 30 digitizes two streams of data, one corresponding to baseline counterpressure data, and one corresponding to pressure pulsation data.

Data emanating from converter 30, is processed by a microprocessor 31 having suitable memory capacity—this microprocessor being operated by programs which will be described in the discussion of FIG. 3.

Continuing the description of FIG. 1, pressure signal data from converter 30 are processed by microprocessor 31 in accordance with the important steps of the present invention. Most of the remaining blocks in FIG. 1 depict generally the software or program which directs the operation of the microprocessor.

In general terms the microprocessor examines the data streams arriving from converter 30 and, throughout the performance of a complete monitoring cycle of blood pressure, exercises various functions on this data to verify proper data, and to arrive at maximally accurate useful information. From an overview point of view, once a cycle of operation has begun, and particularly with the data streams emanating from the converter including pulsation data, and as cuff counterpressure is stepped downwardly as will be explained, every single pulsation which is sensed by the microprocessor has applied to it what is referred to herein as a first artifact rejection technique which is designed to determine that that particular pulsation, or signal, is one which has been induced by blood-pressure activity. For a comprehensive description of applicants' first artifact rejection technique, reference is made to the abovementioned pending patent application, the text and drawings of which are hereby incorporated herein by reference.

Throughout the cycle, every pulse which is so "validated" has, in the particular system now being described, an area integration performed with respect to it to develop waveform integrals upon which the microprocessor then performs other functions to arrive at the finally accepted and usable waveform-specific area data.

In accordance with applicant's NIBP system, three waveforms (distinct groups of pulsation data) are accepted in each of the first two successively reduced counterpressure levels wherein pulses are detected and, as will be explained, a selection and averaging function is performed to select an acceptable, ultimately-generated-and-stored piece of waveform-specific area data. These two data, in such first two steps, establish, via operation of the microprocessor, a pattern for employing prediction, in accordance with what has been referred to herein as the second artifact rejection technique, as a way of determining whether subsequently acquired waveform-specific area data is or is not acceptable.

In FIG. 1, block 32 has been identified as the first artifact rejection technique as a way of putting an identifying name on that part of the program which looks at every single data stream reflecting a pressure pulsation to determine whether it is in fact a blood-pressure-induced pulsation. Block 34, identified as the waveform integrator, indicates that part of the program which, with regard to pulses accepted by block 32, performs a waveform area integration. Block 36, identified as the first waveform area data evaluator, represents that part of the program which examines the first two pulsation-data-containing counterpressure stepped levels for the purpose of "setting up" the operation of block 42—the second artifact rejection technique program which is the subject matter of the present invention.

It is this program portion represented by block 42 which discloses the present invention. Specifically, block 42 applies the second technique, including the generation of a prediction curve, the evaluation of waveform area data vis-a-vis its acceptability relative to that curve, and the smoothing of the curve referred to earlier.

Further, microprocessor 31 is directed by the second artifact rejection technique program to process the third and subsequent pulsation-data-containing counterpressure-stepped levels. At the end of the measuring cycle, the microprocessor generates a final curve connecting final, adjusted (by the aforementioned smoothing of the curve) waveform-specific area data for each counterpressure level of the measurement cycle. The second artifact rejection technique program directing the microprocessor during the third and subsequent counterpressure levels will be more fully described in the discussion of FIGS. 2A–2D and FIG. 3.

Still referring to FIG. 1, block 48 has been identified as the blood pressure parameter determiner as a way of putting an identifying name on that part of a program which directs the microprocessor to determine MAP, systolic, and diastolic pressure from the final curve of waveform-specific area data. The way in which the microprocessor determines the desired blood-pressure parameters from the final curve will be described in the discussion of FIG. 2D.

Finally, once the microprocessor has determined the desired blood pressure parameters, the parameters are sent in a digitized, arabic numeral form to a display 50 where the parameters are represented as arabic numerals by a conventional LCD read-out.

Figure 2A:
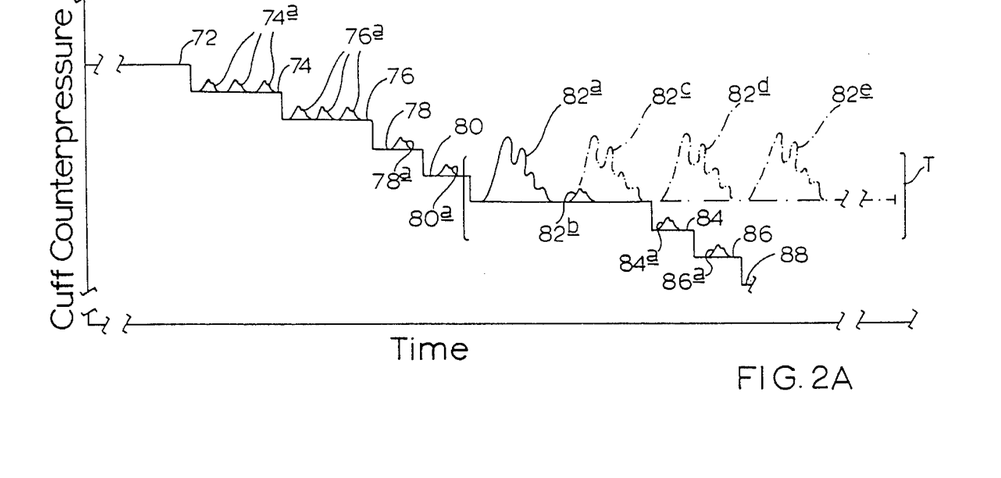
FIG. 2A is a fragmented graph of cuff counterpressure decreasing over time, showing a series of cuff counterpressure levels wherein the waveforms depicted are monitored by the method of the present invention.

Turning now to FIG. 2A, stepped, decreasing cuff counterpressure levels and associated pressure waveforms acquired relative to one measurement are shown in order to depict graphically what has previously been described as first waveform area data evaluator 36 and second artifact rejection technique 42.

Thus, each waveform depicted in FIG. 2A represents pulsation data that has been processed by the microprocessor, seriatim, in order to verify that the data is blood pressure-induced, and to integrate verified data as the data exhibits one of the three aforementioned phases of divergence from baseline counterpressure data.

Finally, after the microprocessor receives pulsation data relative to a point to the right of each waveform's peak, thus at a point where pulsation data is converging to baseline data, the microprocessor stores the integral of each waveform, which is calculated from the previously described waveform base to the waveform processing ending point. Then, waveform integrals for each waveform that the microprocessor verifies and integrates by the aforementioned technique 32 and integrator 34 are further processed to determine one waveform-specific area data value for each counterpressure level.

This further processing of waveform integrals, each representing a series of the aforementioned three phases of pulsation divergence from baseline data, will be described in the discussion of FIGS. 2A–2D and FIG. 3. Referring back to the block diagram of FIG. 1, it is important to note that the remainder of the description of the invention concerns how the microprocessor is directed by what has previously been described as first waveform area data evaluator 36 to determine a waveform-specific area data value for the first two counterpressure levels at which pulsation divergence occurs.

Further, the remainder of the description of the invention concerns how, after the microprocessor determines an area data value for the first two counterpressure levels, the second artifact rejection technique program directs the microprocessor to generate a prediction curve from the two area data values. This prediction curve directs the microprocessor to use a different technique for determining an area data value for the third and subsequent counterpressure levels than the technique of evaluator 36 that was applied to the first two counterpressure levels.

As one final overview point, a significant difference in the two different techniques that the microprocessor uses to determine an area data value for the first two counterpressure levels, and then for the remaining counterpressure levels, is that three pulsation waveforms must be processed at each of the first two levels, whereas generally only one waveform need be processed at the third and subsequent levels.

Referring now to FIG. 2A, as the counterpressure is progressively reduced from a point above systolic pressure to the ending counterpressure, pressure waveforms will occur as discussed in FIG. 1. FIG. 2A depicts no detectable pressure waveforms at a counterpressure level 72 because counterpressure level 72 is above systolic pressure.

As is known in the art, pressure pulsations occur, and corresponding pressure waveforms are monitored even when cuff counterpressure completely occludes vessel 16. However, for some test subjects, pressure pulsations are so weak at a suprasystolic pressure, that their corresponding pressure waveforms are not electronically detectable. Cuff counterpressure level 72 depicts such a situation.

Next, continuing with FIG. 2A and beginning with a counterpressure level 74, verified-to-be-blood-pressure induced waveforms 74a, 74b, 74c are processed by microprocessor 31 (i.e. waveform integrals are developed under the direction of programs 100, 124, 144).

Next, the microprocessor directs valve 22 to decrease counterpressure to a next counterpressure level 76, where the microprocessor processes verified-to-be-blood-pressure induced waveforms 76a, 76b, 76c and develops corresponding waveform integrals.

At each level 74, 76, after the microprocessor develops three waveform integrals for the three waveforms and before counterpressure is decreased, a computer program directs microprocessor 31 to evaluate the three waveform integrals in order to calculate one waveform-specific area data value for each counterpressure level 74, 76.

Next, the calculation used by the microprocessor to determine one area data value from three waveform integrals at either counterpressure levels 74, 76 will be described. Generally, to perform the calculation, the microprocessor chooses the two waveform integrals that are closest to each other, averages the two integrals, and stores a final averaged waveform-specific area data value. The program which directs microprocessor 31 is depicted in FIG. 3.

Figure 3:
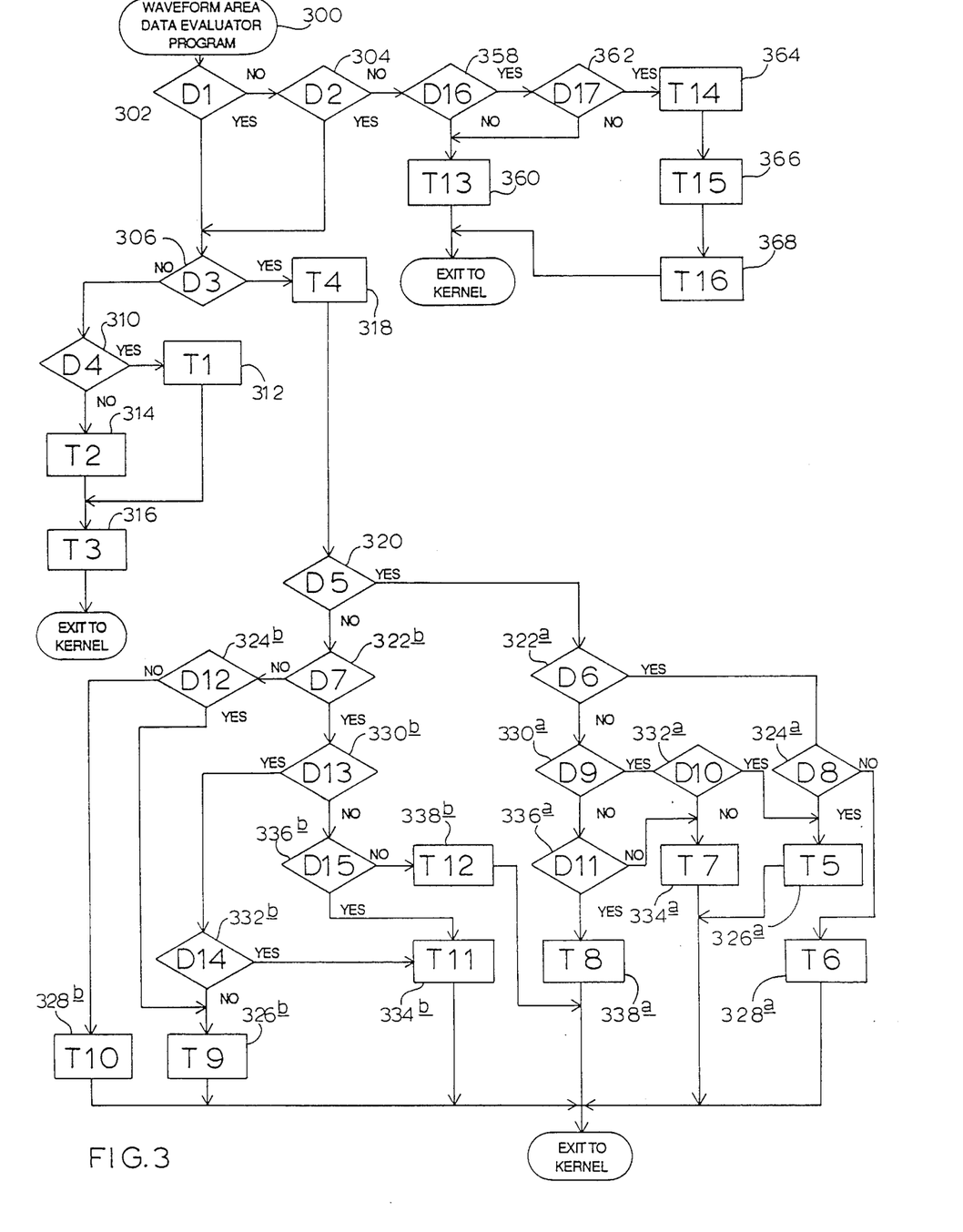
FIG. 3 is a computer-program flow chart further illustrating computer-based implementation of the invention.

Turning now to FIG. 3, in order to determine one waveform-specific area data value for cuff counterpressure level 74, 76, the microprocessor is directed by a portion of Second Artifact Refection Technique 300. This portion has been previously depicted and described as first waveform area data evaluator 36.

The following table is a reference for the immediately following description of FIG. 3, and for the description of FIGS. 2 beginning at page 27:

TABLE V-FIG. 3

| | |
|---|---|
| D1 | Is the Microprocessor Monitoring First Cuff Counterpressure Level? |
| D2 | Is the Microprocessor Monitoring Second Cuff Counterpressure Level? |
| D3 | Has the Microprocessor Developed 2 Waveform Integrals? |
| D4 | Is Sample (N) = 1st Waveform Integral |
| D5 | Is WF1 > WF2? |
| D6 | Is WF2 > WF3? |
| D7 | Is WF2 > WF3? |
| D8 | Is (WF1−WF2) > (WF2 − (WF3?) |
| D9 | Is WF1 > WF3? |
| D10 | Is (WF1 − WF3) > (WF3 − WF2)? |
| D11 | Is (WF3 − WF1) > (WF1 − WF2)? |
| D12 | Is (WF3 − WF2) > (WF2 −WF1)? |
| D13 | Is WF1 > WF3? |
| D14 | Is (WF2 − WF1) > (WF1 − WF3)? |
| D15 | Is (WF2 − WF3) > (WF3 − WF1)? |
| D16 | Is Sample (N) ≦ Upper Bound of Predicted Value |
| D17 | Is Sample (N) ≧ Lower Bound of Predicted Value |
| T1 | Initialize Waveform Integral (N) as WF1 |
| T2 | Initialize Waveform Integral (N) as WF2 |
| T3 | Go to Waveform Beginning Program; Set Program Count = 0 |
| T4 | Initialize Waveform Integral (N) as WF3 |
| T5 | Average WF2 and WF3 = (WF2 + WF3)/2 |
| T6 | Average WF1 and WF2 = (WF1 + WF2)/2 |
| T7 | Average WF1 and WF3 = (WF1 + WF3)/2 |
| T8 | Average WF1 and WF2 = (WF1 + WF2)/2 |
| T9 | Average WF1 and WF2 = (WF1 + WF2)/2 |
| T10 | Average WF2 and WF3 = (WF2 + WF3)/2 |
| T11 | Average WF1 and WF3 = (WF1 + WF3)/2 |
| T12 | Average WF3 and WF2 = (WF3 + WF2)/2 |
| T13 | Go to Waveform Beginning Program; Set Program Count =0 |
| T14 | Store Waveform Integral (N) |
| T15 | Store Baseline Counterpressure (N) |
| T16 | Decrease to next Baseline Counterpressure |

Referring now to FIG. 3, Program 300 begins with decision block 302 (D1) which asks whether the apparatus is at the first cuff counterpressure level at which pulsation values were processed by microprocessor 31. If the answer to decision block 302 (D1) is no, decision block 304 (D2) asks whether the apparatus is at the second cuff counterpressure level at which pulsation values were monitored by microprocessor 31.

Thus, decision blocks 302 (D1) and 304 (D2) direct the microprocessor to determine whether the apparatus is at counterpressure levels such as level 74, 76 depicted in FIG. 2A. If the answer is yes to either decision block 302 (D1) or 304 (D2), then Program 300 directs the microprocessor to evaluate waveform-specific integrals that have been developed at the corresponding first or second cuff counterpressure levels according to what has been previously depicted and described in FIG. 1 as first waveform area data evaluator 36.

Before describing the remainder of FIG. 3, it is important to note that a negative response to decision blocks 302 (D1) and 304 (D2) directs the microprocessor to continue to the portion of the program beginning with decision block 358 (D16). This portion of FIG. 3 describes how Program 300 evaluates waveform integrals that have been developed from pulsation data processed by the microprocessor at counterpressure levels below the first two cuff counterpressure levels. This portion of FIG. 3 will be described after the discussion of FIG. 2B which depicts the generation of what has been previously called a prediction curve, and shows how the microprocessor is directed to use technique 42 to predict an area data value for a next counterpressure level.

Returning back to the yes response to either decision blocks 302 (D1) or 304 (D2) of FIG. 3, decision block 306 (D3) asks whether two waveform integrals have been developed by the microprocessor for the present counterpressure level (e.g. levels 74, 76 of FIG. 2A). If the answer to decision block 306 (D3) is yes, then the present waveform integral is a third integral and Program 300 directs the microprocessor to chose the closest two of the three waveform integrals, average the closest two waveform-specific area data values, and calculate one, averaged waveform-specific area data value for the counterpressure level. The steps of this process begin with task block 318 (T4) and will be described soon. However, the steps that Program 300 follows if the answer to decision block 306 (D3) is no will be described first.

If the answer to decision block 306 (D3) is no, then decision block 310 (D4) asks whether the present waveform integral is the first waveform integral developed by the microprocessor for the present counterpressure level. If the answer to decision block 310 (D4) is yes, then task block 312 (T1) initializes the current waveform-specific area data value as WF1. If the answer to decision block 310 (D4) is no, then the present waveform integral is the second integral and task block 314 (T2) initializes the present waveform integral as WF2.

Next, once the present waveform integral has been initialized by the microprocessor, task block 316 (T3) labels the program for Waveform Beginning Program 200 and the program exits to Kernel 108 so that microprocessor 31 can go to Waveform Beginning Program 200 and develop a next integral for a next processed waveform.

Returning back to the flow diagram, when there is a yes response to decision block 306 (D3), task block 318 (T4) initializes the present waveform integral as WF3. The remainder of FIG. 3 shows the steps that Program 300 follows in order to chose the closest two of the three integrals of the present counterpressure level (i.e., levels 74, 76 of FIG. 2A).

Moving from task block 318 (T4) decision block 320 (D5) asks whether WF1 is greater than WF2. If the answer to decision block 320 (D5) is yes, then decision block 322a (D6) asks whether WF2 is greater than WF3. If the answer to decision block 320 (D5) is no, then decision block 322b (D7) asks whether WF2 is greater than WF3.

As shown in FIG. 3, once Program 300 reaches decision blocks 322a (D6) or 322b (D7), the remaining steps after decision blocks 322a (D6) or 322b (D7) will follow one of twelve paths based on the relative values for WF1, WF2, WF3. First, the six alternate paths that are possible after decision block 322a (D6) will be discussed. Then, the six paths that are possible after decision block 322b (D7) will be discussed.

If the answer to decision block 322a (D6) is yes, then decision block 324a (D8) asks whether (WF1−WF2) is greater than (WF2−WF3). Continuing on with the flow diagram after block 324a before returning to the possibility of a negative answer to decision block 322a (D6), a yes or a no answer to decision block 324a (D8) allows Program 300 to decide which two of WF1, WF2, WF3 are the closest to each other. If the answer to decision block 324a is yes, then WF2 and WF3 are the two closest area data values, and task block 326a (T5) averages WF2 and WF3 in order to calculate one waveform-specific area data value for the current cuff counterpressure level. If the answer to decision block 324a (D8) is no, then WF1 and WF2 are the two closest area data values and task block 328a (T6) calculates an average waveform-specific area data value for the current cuff counterpressure level.

Returning now to the possibility of a negative answer to decision block 322, decision block 330a (D9) asks whether WF1 is greater than WF3. If the answer to decision block 330a (D9) is yes, then decision block 332a (D10) asks whether (WF1−WF3) is greater than (WF3−WF2).

Again the description will continue with steps following decision block 332a (D10) before describing the possibility of a negative answer to decision block 330a (D9). If the answer to decision block 332a (D10) is yes, then WF2 and WF3 are the two closest area data values and task block 326a (T5) would calculate an average waveform-specific area data value for the current cuff counterpressure level. If the answer to decision block 332a (D10) is no, then WF1 and WF3 are the two closest area data values and task block 334a (T7) would calculate an average waveform-specific area data value from WF1 and WF3.

Returning now to the possibility of a negative answer to decision block 330a (D9), decision block 336a (D11) asks whether (WF3−WF1) is greater than (WF1−WF2). If the answer to decision block 336a (D11) is yes, then WF1 and WF2 are the two closest area data values and task block 338a (T8) calculates an average waveform-specific area data value from WF1 and WF2. If the answer to decision block 336a (D11) is no, then WF1 and WF3 are the two closest area data values and task block 334a (T7) would calculate an average waveform-specific area data value from WF1 and WF3.

Returning to the possibility of a negative answer to decision block 320 (D5), decision block 322b (D7) asks whether WF2 is greater than WF3. If the answer to decision block 322b (D7) is no, then decision block 324b (D12) asks whether (WF3−WF2) is greater than (WF2−WF1). If the answer to decision block 324b (D12) is yes, then WF1 and WF2 are two closest area data values and task block 326b (T9) calculates and stores an average waveform-specific area data value based on WF1 and WF2. If the answer to decision block 324b (D12) is no, then WF2 and WF3 are the two closest area data values and task block 328b (T10) calculates and stores an average waveform-specific area data value from WF2 and WF3.

Returning now to the possibility of a positive answer to decision block 322b (D7), decision block 330b (D13) asks whether WF1 is greater than WF3. If the answer to decision block 330b (D13) is yes, then decision block 332b (D14) asks whether (WF2−WF1) is greater than (WF1−WF3). Again, the description will continue with the steps after decision block 332 before describing the possibility of a negative answer to decision block 330b (D13). If the answer to decision block 332b (D14) is no, then WF1 and WF2 are the two closest area data values and decision block 326b (T9) calculates and stores an average waveform-specific area data value based on WF1 and WF2. If the answer to decision block 332b (D14) is yes, then WF1 and WF3 are the two closest area data values and task block 334b (T11) calculates and stores an average waveform-specific area data value from WF1 and WF3.

Next, returning to possibility of a negative answer to decision block 330b (D13), decision block 336b (D15) asks whether (WF2−WF3) is greater than (WF3−WF1). If the answer to decision block 336b (D15) is yes, then task block 334b (T11) calculates and stores an average, waveform-specific area data value from WF1 and WF3. If the answer to decision block 336b (D15) is no, then WF3 and WF2 are the two closest area data values and task block 338b. (T12) calculates an average, waveform-specific area data value from WF3 and WF2.

Finally, after task blocks 326a (T5), 326b (T9), 328a (T6), 328b (T10), 334a (T7), 334b (T11), 338a (T8), or 338b (T12) calculate and store an average waveform-specific area data value, Program 300 exits to Kernel 108 so that the microprocessor can go to the programs described in U.S. patent application Ser. No. 07/198,468 to develop a next waveform integral from pulsation data divergence at a next counterpressure level.

Referring back to FIG. 2A, after the microprocessor determines a waveform-specific area data value for counterpressure levels 74, 76, what has previously been described as second artifact rejection technique 42 directs the microprocessor to generate a prediction curve using the area data values of counterpressure levels 74, 76. This prediction curve, and the corresponding predictive algorithm included in what has previously been described as second artifact rejection technique 42 will be explained later in the description of FIGS. 2B, 2C.

However, to describe generally what happens, at cuff counterpressure level 76, the microprocessor is directed by a program employing second artifact rejection technique 42 to predict an expected-to-be-stored waveform-specific area data value for a pressure waveform that as yet, has not been processed at a next counterpressure level 78. The microprocessor makes this prediction from a prediction curve that the microprocessor generated from the area data values of levels 74, 76.

Referring to FIG. 2A, blood pressure induced waveform 78a represents a waveform that is actually processed by Microprocessor 31 at counterpressure level 78 A waveform integral developed from measured waveform 78a by the method disclosed in the above-referenced patent application is now evaluated by whether it meets the criterion of the predicted waveform-specific area data value generated by the microprocessor under the direction of second artifact rejection technique 42. The evaluation includes checking whether the waveform integral of waveform 78a is within the upper and lower bounds of the corresponding predicted waveform-specific area data value generated by the microprocessor under the direction of second artifact rejection technique 42.

In order to explain how the microprocessor evaluates the waveform integral of waveform 78a, reference is now made to FIG. 3, and specifically to the portion of the waveform area data evaluator program beginning with decision block 358 (D16). Referring back to the previous discussion of FIG. 3, it is important to note that program 300 does not direct the microprocessor to decision block 358 (D16) unless the answer to decision blocks 302 (D1), 304 (D2) is no. Thus, program 300 only directs the microprocessor to the portion of program 300 beginning with decision block 358 (D16) when the microprocessor is processing data at the third and following counterpressure levels.

The portion of Program 300 which directs the microprocessor's evaluation of waveform integrals developed from pulsation waveforms occurring at the third and subsequent counterpressure levels will be discussed after the description of FIG. 2B because FIG. 2B explains how the microprocessor is directed by second artifact rejection technique 42 to predict an expected-to-be-stored waveform-specific area data value for the third and subsequent counterpressure levels. Because it is first necessary to understand the prediction of area data values using second artifact rejection technique 42, the explanation of how program 300 uses the predicted area data value of technique 42 will be postponed until after the description of technique 42 in FIG. 2B.

Still referring to FIG. 2A, it is sufficient for now to keep in mind that program 300 uses a different method of determining one waveform-specific area data value for counterpressure levels 78–86 than the previously described method of determining one area data value for counterpressure levels 74, 76. Therefore, with the exclusion of counterpressure level 82, the remainder of FIG. 2A depicts how the present invention would continue the measurement cycle if the waveform integral developed by the microprocessor for pressure waveforms at each counterpressure level met the criterion set by the predicted area data value for each corresponding counterpressure level.

Thus, after program 300 determined one area data value for counterpressure level 78 by a portion of the program yet to be described, the microprocessor directs valve 22 to reduce counterpressure to a next counterpressure level 80.

Next, the aforementioned, and yet to be further explained, prediction and determination process would be repeated at counterpressure level 80. The process would repeat for subsequent counterpressure levels provided each waveform integral of each pulsation waveform at each subsequent cuff counterpressure level fell within the bounds of a predicted waveform-specific area data value (predicted by the microprocessor under the direction of second artifact rejection technique 42).

Further, FIG. 2A shows how the present invention responds when a waveform integral of a pulsation waveform occurring at a counterpressure level does not fall within the bounds of a previously predicted area data value. A counterpressure level 82 is shown with five blood pressure induced waveforms 82a–82e depicted thereon. Waveforms 82a, 82b are shown by solid lines in order to show a first scenario. Then, blood pressure induced waveform 82c is depicted by dot-dashed lines to represent a second scenario wherein waveform 82c occurs instead of waveform 82b, and further, wherein waveforms 82d, 82e would also occur at cuff counterpressure level 82.

First, the first scenario in which blood pressure induced waveforms 82a, 82b occur will be described. After microprocessor 31 develops a waveform integral of waveform 82a, Program 300 determines if the waveform integral is within the bounds of its corresponding predicted area data value. Further, FIG. 2A depicts waveform 82a as larger than previously accepted waveforms 78a, 80a in order to graphically represent that the developed waveform integral of waveform 82a is outside the bounds of the corresponding predicted waveform-specific area data value of waveform 82a.

Thus, Program 300 rejects the waveform integral of waveform 82a because the value is outside the bounds of the previously predicted waveform-specific area data value for waveform 82a. In this specific case, because waveform 82a is substantially larger than previously accepted waveforms 78a, 80a, the developed waveform integral of waveform 82a would be rejected by the microprocessor under the direction of Program 300 because it is greater than the upper bounds of the previously predicted waveform-specific area data value for waveform 82a. Again, the way in which Program 300 of FIG. 3 determines whether to accept the waveform integral at the third and subsequent counterpressure levels will be described following the description of FIG. 2B.

However, unlike its depiction in FIG. 2A, it is also possible that waveform 82a could be substantially smaller than previously accepted waveform 78a, 80a. Then, the developed waveform integral for this hypothetical, undepicted waveform 82a would be rejected by the microprocessor because the measured area data value would be outside the lower bounds of the previously predicted waveform-specific area data value for this hypothetical, undepicted waveform 82a.

Next, returning to the point where the microprocessor rejects the waveform integral of waveform 82a, the microprocessor directs valve 22 to stay at counterpressure level 82. Then, microprocessor 31 develops a waveform integral of a next-occurring waveform 82b according to the method described in application, Ser. No. 07/198,468. Then, the microprocessor determines whether the integral of waveform 82b is within the bounds of its corresponding predicted area data value (remember that microprocessor 31 predicts the area data value according to technique 42 and determines whether to accept the integral of waveform 82b under the direction of yet-to-be-described portion of Program 300).

As depicted in FIG. 2A, waveform 82b is substantially the same size as previously accepted waveforms 78a, 80a. This graphically depicts that the integral of waveform 82b is accepted by the microprocessor because the measured area data value falls within the bounds of the predicted waveform-specific area data value.

Then, upon acceptance of the waveform-specific area data value for waveform 82b by microprocessor 31, the microprocessor directs valve 22 to reduce counterpressure by a next increment. The same process would repeat, including predicting a subsequent, expected-to-be-stored waveform-specific area data value, developing a waveform integral for a next-occurring pressure waveform, and determining whether the waveform integral of the waveform falls within the bounds of the predicted waveform-specific area data value.

Finally, remaining at counterpressure level 82 of FIG. 2A, the second scenario will be described in which waveform 82b does not occur, but rather waveforms 82c, 82d, 82e occur and corresponding waveform integrals are developed by microprocessor 31.

FIG. 2A depicts waveforms 82c, 82d, 82e as also substantially larger than previously accepted waveforms 78a, 80a in order to graphically depict that the corresponding, developed waveform integrals of waveforms 82c, 82d, 82e are outside the bounds of the corresponding predicted area data value for counterpressure level 82. Thus, microprocessor 31 would reject the waveform integrals of waveforms 82c, 82d, 82e because the measured area data values would be outside the bounds of the predicted area data value.

Further, the microprocessor directs valve 22 to stay at counterpressure level 82 and continues to develop waveform integrals for subsequently occurring pulsation waveforms.

Further, FIG. 2A depicts a fragmented portion of counterpressure level 82 by dot-dashed lines in order to show that the aforementioned, developing, predicting, and determining steps carried out by microprocessor 31 under the direction of the corresponding programs would repeat, until either a developed waveform integral of a waveform was accepted by the microprocessor because it was within the bounds of the predicted area data value, or until time period "T" occurred as shown in FIG. 2A.

If time period "T" occurs without the microprocessor having accepted a waveform integral of a subsequently occurring waveform at counterpressure level 82, then the apparatus would abort the entire measuring cycle, and the microprocessor would direct valve 22 to deflate cuff 14. Currently, the preferred practice of the present invention is to use a 30 second time period as time "T".

Figure 2B:
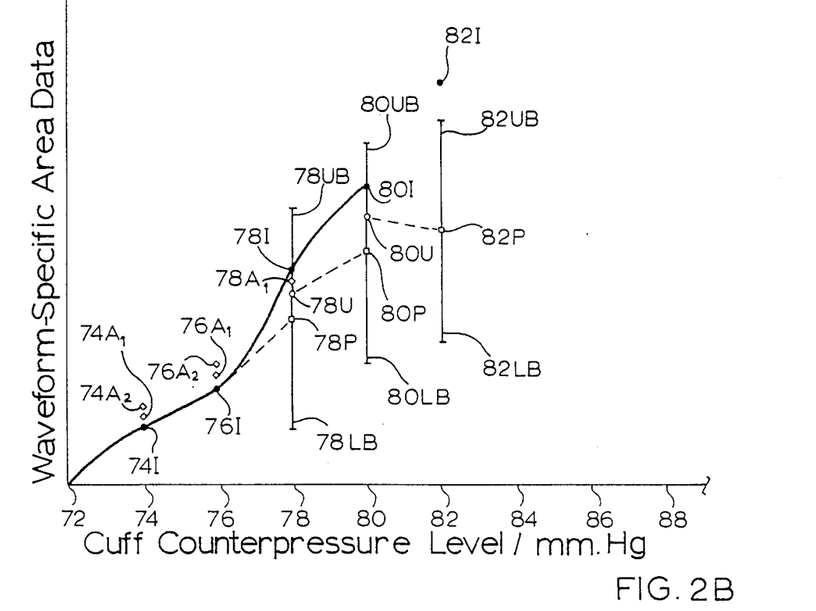
FIG. 2B is a fragmented graph of waveform-specific data vs. cuff counterpressure levels that depicts how the method technique of the invention predicts a subsequent, expected-to-be-stored waveform data value for a subsequent cuff counterpressure level.
Figure 2C:
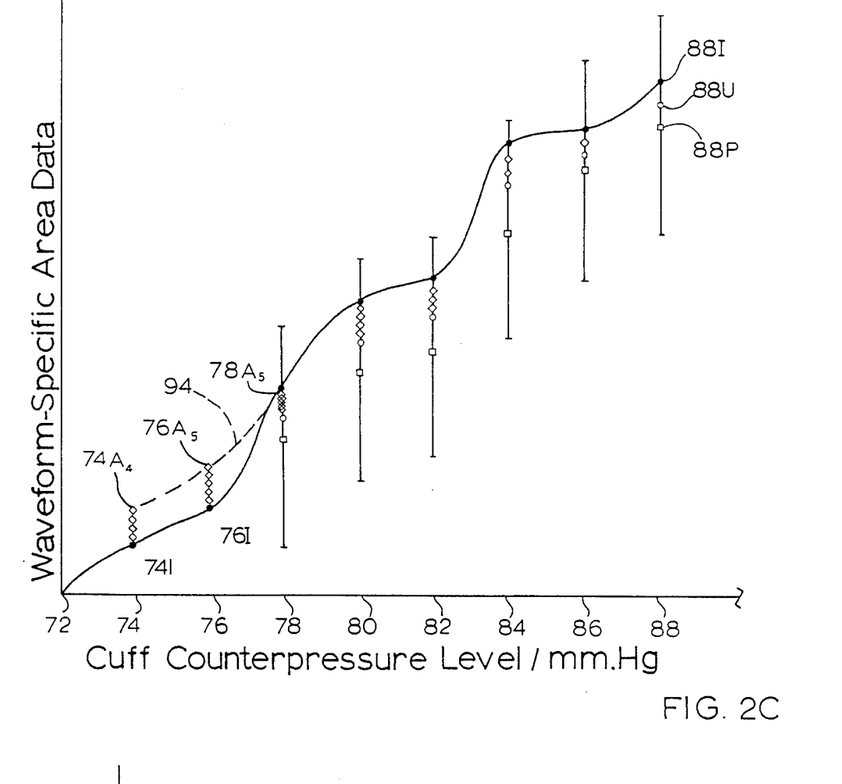
FIG. 2C is a fragmented graph of waveform data vs. cuff counterpressure levels illustrating the "smoothing" technique referred to earlier.
Figure 2D:
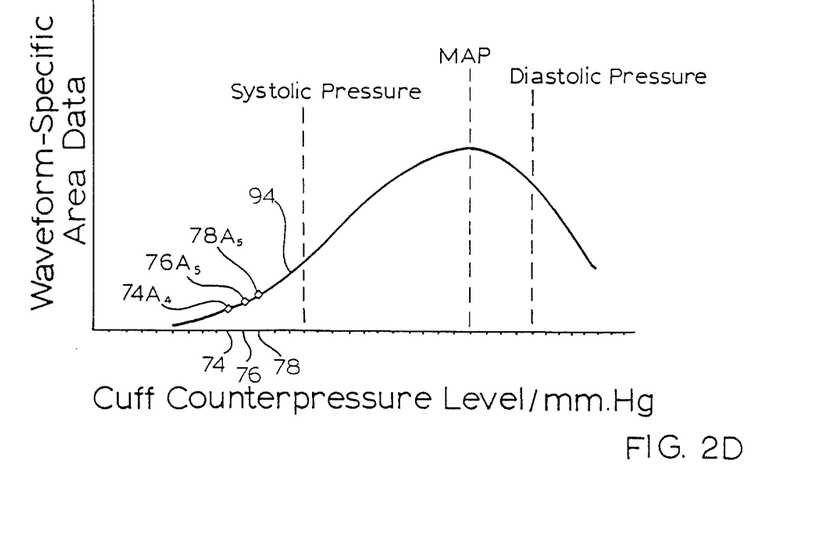
FIG. 2D is a graph of waveform-specific data vs. cuff counterpressure levels for an entire measuring cycle of a living test subject.

Turning now to FIGS. 2B–2D, three graphs of waveform-specific area data values vs. cuff counterpressure levels are shown. FIGS. 2B and 2C are fragmented graphs wherein the vertical spread of points are exaggerated in order to graphically depict the operation of second artifact rejection technique 42 and data smoother 46.

Turning first to FIG. 2B, cuff counterpressure levels 72–82 are shown wherein solid points 74I–82I correspond to developed waveform integrals for each counterpressure level. Further, referring to FIG. 2B, solid points 74I and 76I also correspond to stored waveform-specific area data values determined by microprocessor 31 for counterpressure levels 74, 76 according to the previously described portion of Program 300 of FIG. 3. There is no corresponding waveform-specific area data value for cuff counterpressure level 72 because, as discussed in FIG. 2A, no blood pressure induced waveform occurred at counterpressure level 72 because it was above systolic pressure.

Referring now to counterpressure level 78 of FIG. 2B, second artifact rejection technique 42 directs the microprocessor to predict a subsequent, expected-to-be-stored waveform-specific area data value 78P. The specific algorithms used to predict subsequent, expected-to-be-stored waveform-specific area data are called Kalman equations because they are based on the previously noted "Kalman Filter theory" For a discussion of the Kalman equations necessary to second artifact rejection technique 42, see Geld, Arthur, *Applied Optimal Estimation*, MIT Press, 1974.

Briefly, applicants' utilization of Kalman Filter theory involves multiplying what is known as a state vector by what is known as the state transition matrix. This multiplication is the algorithm by which applicants achieve "pulse prediction" and "pulse adjustment". Applicants define the state vector as:

$$X = [A_i, A_{i-1}, A_{s1}, A_{s2}, A_{s3}]T$$

where: $A_i$, $A_{i-1}$ are waveform-specific data values at the current and previous cuff counterpressure levels, i.e. occurring at times $T_i$ and $T_{i-1}$; and $A_{s1}$, $A_{s2}$, and $A_{s3}$ are the first, second, and third estimates of $A_{i-1}$ based on what has been described as data "smoothing".

Concerning the state transition matrix (STM), Geld states that it is a 6×6 matrix defined as:

$$STM = \begin{matrix} a & b & 0 & 0 & 0 & 0 \\ 1 & 0 & 0 & 0 & 0 & 0 \\ 1 & 0 & 0 & 0 & 0 & 0 \\ 0 & 1 & 0 & 0 & 0 & 0 \\ 0 & 0 & 1 & 0 & 0 & 0 \\ 0 & 0 & 0 & 1 & 0 & 0 \end{matrix}$$

where "a" and "b" are constants, and two ×2 identity matrices are included, one identity matrix provided in the first and second columns of the third and fourth rows, and one identity matrix provided in the third and fourth columns of the fifth and sixth rows.

The identity matrices augment the state transition matrix to provide for what is known in the art as "fixed lag smoothing". For a discussion of the algorithms that are used in the invention to direct the microprocessor's data adjustments, see the discussion of fixed lag smoothing in Ch. 7.3 of Anderson and Moore, *Estimation Theory*, Prentice Hall, 1979.

Applicants modified the state transition matrix to a 5×5 matrix defined as:

$$STM = \begin{matrix} a & b & 0 & 0 & 0 \\ 1 & 0 & 0 & 0 & 0 \\ 0 & 1 & 0 & 0 & 0 \\ 0 & 0 & 1 & 0 & 0 \\ 0 & 0 & 0 & 1 & 0 \end{matrix}$$

where "a" and "b" are constants based on a second order critically damped model of the system, and two identity matrices are provided, one in the first and second columns of the second and third row, and one in the third and fourth columns of the fourth and fifth rows.

By using Kalman Filter theory, a second artifact rejection technique program directs the microprocessor to predict value 78P based on a prediction curve that microprocessor 31 generates from area data values 74, 76.

Then, the second artifact rejection technique program directs the microprocessor to set upper and lower bounds for predicted waveform-specific area data value 78P. These bounds are shown by upper bound bar 78UB and lower bound bar 78LB. Next, the microprocessor develops a waveform integral 78I of pulsation waveform 78a (depicted in FIG. 2A). Then, microprocessor 31 checks, under the direction of soon-to-be-described portion of program 300, whether developed waveform integral 78I is within upper bounds 78UB and lower bounds 78LB As shown in FIG. 2B, second waveform area data evaluator 38 accepts waveform-specific area data value 78I because it falls within upper bounds 78UB and lower bounds 78LB.

Next, second artifact rejection technique program directs the microprocessor to calculate updated area data value 78U based on the difference between waveform integral 78I and predicted area data value 78P. Further, the microprocessor adjusts area data values 74I, 76I so that a first (undepicted) smoothed curve is generated through adjusted waveform-specific area data values $74A_1$, $76A_1$, and updated waveform-specific area data value 78U.

Next, the microprocessor repeats the process for cuff counterpressure level 80. Again, the microprocessor, under the direction of the second artifact rejection technique program accepts a developed waveform integral 80I because it falls within upper bounds 80UB and lower bounds 80LB of predicted, expected-to-be-stored waveform-specific area data value 80P. Then, the microprocessor calculates an updated area data value 80U, and adjusts once-adjusted area data values 74A, 76A, of counterpressure levels 74, 76 to twice-adjusted area data values $74A_2$, $76A_2$. Also, the microprocessor adjusts value 78I to value $78A_1$. Finally, the microprocessor generates a second (undepicted) adjusted curve through points $74A_2$, $76A_2$, and $78A_1$.

Next, the microprocessor predicts a subsequent, expected-to-be-stored waveform-specific area data value 82P for cuff counterpressure level 82. However, the microprocessor does not accept developed waveform integral 82I because it is outside upper bound 82UB of predicted waveform-specific area data value 82P.

Referring back to FIG. 2A, the microprocessor then develops an integral of second waveform 82b at counterpressure level 82. Further, the microprocessor checks whether the developed integral of waveform 82b was within bounds 82UB, 82LB. If, as shown in the first scenario of FIG. 2A at counterpressure level 82, waveform 82B was processed, and its developed integral was within bounds 82UB, 82LB, then microprocessor directs valve 22 to decrease counterpressure to next level 84.

However, if the second scenario depicted at counterpressure level 82 and FIG. A occurred, then the microprocessor rejects developed integrals of pulsation waveforms 82C-82E because they are outside bounds 82UB, 82LB.

Next, the portion of program 300 that directs the microprocessor to determine a final area data value for the third and subsequent counterpressure levels (shown in FIG. 2A as levels 78-86) will be described. Thus, turning to FIG. 3, attention is directed to decision block 358 (D16) which is the decision block the microprocessor is directed to if counterpressure is at the third or subsequent counterpressure levels.

Referring to FIG. 3, decision block 358 (D16) asks whether a waveform integral developed by the microprocessor for a pulsation waveform is less than or equal to the upper bounds of the present counterpressure level's predicted waveform-specific area data value. In order to graphically depict what decision block 358 (D16) concerns, reference is made to the discussion of predicted waveform-specific area data value 78P of cuff counterpressure level 78 depicted in FIG. 2B. Thus, the reference to a predicted area data value and the upper bounds of a predicted area data value in decision block 358 (D16) refers to values 78P and 78UB of FIG. 2B.

If the answer to decision block 358 (D16) is no, then task block 360 (T13) labels the program for Waveform Beginning Program 200 and the program exits to Kernel so that microprocessor 31 will monitor a next blood pressure induced waveform at the same, present counterpressure level. Again, reference is made to FIG. 2B and FIG. 2A. Specifically, referring to counterpressure level 82, the microprocessor processes waveform 82A of FIG. 2A and develops a waveform integral represented by point 82I of FIG. 2B. Further, integral 82I is outside upper bounds 82UB of predicted area data value 82P. This, event graphically depicts what happens when the answer to decision block 358 (D16) is no. Thus, task block 360 (T13) labels the program for Waveform Beginning Program 200 so that a next waveform will be processed at counterpressure level 82. This next waveform is shown as waveform 82B of FIG. 2A.

Continuing with the discussion of decision block 358 (D16), if the answer to decision block 358 (D16) is yes, then decision block 362 (D17) asks whether the present, developed waveform integral is greater than or equal to the lower bounds of the present counterpressure level's predicted area data value. If the answer to decision block 362 (D17) is no, then task block 360 (T13) again labels the program for Waveform Beginning Program 200 and the program exits to Kernel so that microprocessor 31 will process a next pulsation waveform at the present counterpressure level. Again, reference is made to FIG. 2B, and specifically to lower bounds 78LB of predicted waveform-specific area data value 78P of cuff counterpressure level 78 for an example of the lower bounds criterion represented in decision block 362 (D17).

If the answer to decision block 362 (D17) is yes, then the developed waveform integral for the present counterpressure level is accepted. Thus, task block 364 (T14) stores the integral as the waveform-specific area data value for the counterpressure level, and task block 366 (T15) stores the corresponding counterpressure level value at which the pulsation waveform represented by the integral occurred. Finally, task block 368 (T16) labels the program ready for a next counterpressure level and the program exits to Kernel 308 so that microprocessor 31 will signal pressure control 44 to decrease counterpressure by a next increment of $5\frac{1}{3}$-mm Hg.

Turning now to FIG. 2C, a second fragmented graph of waveform-specific area data vs. cuff counterpressure levels is shown wherein corresponding predicted, developed, updated, and adjusted waveform-specific area data values are calculated and developed by the process outlined in the discussion of FIG. 2B. According to the preferred method of practicing the present invention, the microprocessor adjusts waveform-specific area data values for counterpressure levels relative to a present counterpressure level.

The adjustment is made in "forward"- and "backward"- looking fashion. Thus, area data values for previous counterpressure levels are adjusted ("backward-looking"), and a predicted area data value for a next, yet-to-be-monitored counterpressure level is adjusted ("forward-looking"). While different numbers of area data values can be chosen for adjustment treatment, say in the range of about three to five, in the method disclosed herein, five previous counterpressure levels are adjusted.

Thus, for example, when the second artifact rejection technique program directs the microprocessor to calculate an updated waveform-specific area data value 88U for cuff counterpressure level 88, the microprocessor adjusts the area data values of the five previous counterpressure levels 78, 80, 82, 84, 86. Therefore, adjusted waveform-specific area data value 78A5 is the final waveform-specific area data value for counterpressure level 78.

Further, adjusted waveform-specific area data values 74A4 and 76A5 are the final waveform-specific area data values for counterpressure levels 74, 76, respectively. Thus, the microprocessor generates a fifth adjusted curve 94 connecting all final waveform-specific area data values. In FIG. 2C, the fifth adjusted curve is partially shown by dot-dashed lines connecting final waveform-specific area data values 74A4, 76A5, and 78A5.

Turning now to FIG. 2D, a graph of waveform-specific area data vs. cuff counterpressure levels for the entire measurement cycle of living test subject 18 is shown. After monitoring the ending counterpressure level, the microprocessor generates fifth adjusted curve 94 for the final waveform-specific area data values of each counterpressure level monitored. For example, fifth adjusted curve 94 passes through final waveform-specific area data values 74A4, 76A5, and 78A5 of counterpressure levels 74, 76, 78, respectively.

Next, the microprocessor is directed by a program to determine desired blood pressure parameters by what has previously been described as determiner 48. First, the microprocessor determines MAP as the lowest counterpressure level with the greatest final area data value. Further, the microprocessor determines the systolic and diastolic pressure of subject 18 as the counterpressure levels corresponding to waveform-specific area data values of fifth adjusted curve 94 that have an experimentally determined fractional relationship with the greatest area data value corresponding to MAP.

Systolic pressure is determined herein as the counterpressure level above MAP corresponding to the waveform-specific area data value on fifth adjusted curve 94 that is sixty percent of the MAP waveform-specific area data value. Diastolic pressure is determined as the waveform-specific area data value corresponding to a counterpressure level below MAP wherein the area data value on fifth adjusted curve 94 is eighty percent of the value of the MAP waveform-specific area data value.

In conclusion, the method of the present invention employs a unique technique of "pulse-prediction" and "pulse-adjustment" after development of waveform data values for a predetermined number of cuff counterpressure levels at the beginning of a blood pressure measuring cycle. Using the "pulse-prediction" technique, a next, expected-to-be-encountered data value for a next, lower cuff counterpressure level is predicted. Next, a waveform data value is developed for an actually measured waveform at the next cuff counterpressure level, and this waveform data value is checked for acceptability as bloodpressure induced data by determining whether the waveform data value is within experimentally set upper and lower bounds of its corresponding predicted value. If the waveform data value that is developed from the measured waveform is not within such experimentally set bounds of the predicted value, the developed data value is rejected as indicating false, or artifact, data. In such a case, an additional waveform is measured, a waveform data value is developed, and another "data-acceptability" check is made by checking whether the data value is within the predicted value's experimentally set bounds. In the situation where a waveform data value developed from a measured waveform is within the predicted value's experimentally set bounds, the preferred practice of the present invention is to decrease counterpressure to a next level and repeat the above-described steps.

Additionally, the preferred practice of the present invention employs "pulse-adjustment" by adjusting previously developed and stored waveform data values based on the difference between a measured waveform data value and a corresponding predicted waveform data value for a given cuff counterpressure level. Such "pulse-adjustment" can be used to "smooth" the above-described curve that has been fitted from previously developed waveform data values.

As a result of the above-described "pulse-prediction" and "pulse-adjustment", a final curve of "smoothed" data is generated. Applicants have found that the present invention significantly enhances the likelihood that a false data pulse will be rejected as artifact, and therefore, that the resulting final curve of waveform data values are more likely to be bloodpressure induced data values. Thus, determining systolic, diastolic, and MAP from such data of increased reliability, result in bloodpressure parameters of increased reliability.

While a preferred method of practicing the invention has been disclosed, it should be appreciated that variations and modifications may be made thereto without departing from the spirit of the invention.

It is claimed and desired to secure by Letters Patent:

1. An artifact rejection method for noninvasive blood-pressure measurement employed to predict data acquired relative to blood-pressure-induced pressure waveforms, said method comprising, in a means for producing a baseline counterpressure adjacent a blood vessel in a living subject, progressively reducing such counterpressure in counterpressure steps from a predetermining beginning, occluding baseline counterpressure above systolic pressure to a predetermined ending baseline counterpressure;

during said reducing, and for a predetermined number of such counterpressure steps, and at each such step, monitoring a plurality of the waveforms of blood-pressure-induced changes in the pressure of such means;

on the basis of said monitoring, developing and storing waveform-specific data;

at each of such counterpressure steps, choosing a predetermined number of stored, waveform-specific data values as indicative of blood pressure and computing one waveform-specific value from such chosen values;

thereafter, from such computed values, fitting a curve on a step-by-step basis and, from such curve, predicting an expected-to-be-stored waveform-specific data value for a next baseline counterpressure step, and applying experimentally determined bounds to such expected-to-be-stored waveform-specific data value;

modifying said monitoring at such next baseline counterpressure step so that a single, first waveform-specific data value is developed and stored; and checking whether such single, first value is within such bounds from said predicting as a way of determining the acceptability of the value.

2. The method of claim 1, wherein, during said reducing, said monitoring of waveforms is done for two counterpressure steps.

3. The method of claim 1, wherein said developing and storing involves developing and storing waveform-specific area data.

4. The method of claim 1, wherein said choosing includes choosing three waveform-specific data values as the predetermined number of stored data values.

5. The method of claim 1, wherein said computing includes averaging such chosen waveform-specific data values.

6. The method of claim 1, wherein a Kalman filter is employed to predict such expected-to-be-stored data values.

7. The method of claim 1, further including the step of adjusting a predetermined number of previously stored waveform-specific data values by utilizing subsequent, developed waveform-specific data values.

8. The method of claim 7, wherein said adjusting is done to three to five previously stored data values.

9. The method of claim 8, wherein a Kalman filter is employed to adjust previously stored waveform-specific data values.

10. The method of claim 7, wherein said adjusting is done simultaneously with said predicting.

11. The method of claim 1, wherein, if such single, first value is outside such bounds, said checking includes repeating said steps of monitoring, developing, storing, and checking a next waveform-specific data value at such next counterpressure step.

12. The method of claim 11, wherein, if subsequently monitored, developed, stored, and checked data values of such next counterpressure step are outside such bounds, and a predetermined time period has elapsed, said repeating is omitted.

13. The method of claim 12, wherein such time period is about 30-seconds.

14. A data-curve-smoothing artifact refection method for noninvasive blood-pressure measurement employed to adjust previously stored data acquired relative to blood-pressure-induced pressure waveforms, said method comprising, in a means for producing a baseline counterpressure adjacent a blood vessel in a living subject, progressively reducing such counterpressure in counterpressure steps from a predetermined beginning, occluding baseline counterpressure above systolic pressure to a predetermined ending baseline counterpressure;

during said reducing, and for a predetermined number of such counterpressure steps, and at each such step, monitoring a plurality of the waveforms of blood-pressure-induced changes in the pressure of such means;

on the basis of said monitoring, developing and storing waveform-specific data;

at each of such counterpressure steps, choosing a predetermined number of stored, waveform-specific data values as indicative of blood pressure and computing one waveform-specific data value from such chosen values;

thereafter, from such computed values, fitting a curve on a step-by-step basis and, from such a curve, adjusting previously stored waveform-specific data values by utilizing subsequent, developed data values, as a way of smoothing the curve.

15. The method of claim 14, wherein, during said reducing, said monitoring of waveforms is done for two counterpressure steps.

16. The method of claim 14, wherein said developing and storing involves developing and storing waveform-specific area data.

17. The method of claim 14, wherein said choosing includes choosing three waveform-specific data values as the predetermined number of stored data values.

18. The method of claim 14, wherein said computing includes averaging such chosen waveform-specific values.

19. The method of claim 14, wherein a Kalman filter is employed to adjust previously stored data values.

* * * * *